US00PP23555P2

(12) United States Plant Patent
Kordes

(10) Patent No.: US PP23,555 P2
(45) Date of Patent: Apr. 23, 2013

(54) FLORIBUNDA ROSE PLANT NAMED 'KORFRIEDHAR'

(50) Latin Name: *Rosa hybrida*
Varietal Denomination: KORfriedhar

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/135,651

(22) Filed: Jul. 11, 2011

(51) Int. Cl.
*A01H 5/00* (2006.01)

(52) U.S. Cl. ..... Plt./141

(58) Field of Classification Search ..... Plt./141, Plt./148

See application file for complete search history.

*Primary Examiner* — Kent L Bell

(57) ABSTRACT

A new and distinct variety of rose with abundant, novel lavender flowers, and attractive foliage with excellent disease resistance. It exhibits an upright to bushy habit. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfriedhar'.

The new variety of rose plant of the present invention originated from a controlled crossing in a breeding program of two distinct parents during the summer of 2004. The crossing was between an 'un-named seedling', and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfriedhar'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an 'un-named seedling', by the following combination of characteristics:

1. The petal count of 'KORfriedhar' is very double while the petal count of the seed parent is semi-double.
2. The flower size of 'KORfriedhar' is large while the flower size of the seed parent is medium.

The new rose plant may be distinguished from its pollen parent, an 'un-named seedling' by the following combination of characteristics:

1. The flower color of 'KORfriedhar' is lavender while the flower color of the pollen parent is violet.
2. The disease resistance of 'KORfriedhar' is excellent while the disease resistance of the pollen parent is average.

The objective of the hybridization was to create a new and distinct rose plant with unique qualities, such as:

1. Uniform growth and flowering;
2. Abundant attractive, recurrent lavender flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORfriedhar' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfriedhar' was selected in May, 2005 from the seedling beds to be asexually propagated for further evaluation. The first asexual propagation of 'KORfriedhar' was done by budding to seedling understocks in July, 2005 at the inventor's nursery in Offenseth-Sparrieshoop, Germany.

This initial and other subsequent propagations conducted in controlled environments demonstrate that 'KORfriedhar' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORfriedhar'.

DETAILED BOTANICAL DESCRIPTION

The following is a description of 'KORfriedhar', as observed growing in June, 2011 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORsicht', a non-patent rose variety are compared to 'KORfriedhar' in Chart 1.

CHART 1

| Characteristic | 'KORfriedhar' | 'KORsicht' |
|---|---|---|
| Petal count | Very double, 70-75 petals on average | Double, 26-40 petals on average. |
| Disease resistance | Excellent disease resistance. | Average disease resistance. |
| Flower buds per stem | Multiple flower buds, generally 1-5. | Mostly solitary. |
| Average plant height | 80 cm. | 120 cm. |

Parents:

*Seed parent*. —An 'un-named seedling'.

*Pollen parent*.—An 'un-named seedling'.

Classification:

*Botanical classification*.—*Rosa hybrida* 'KORfriedhar'.

*Commercial classification*.—Floribunda rose.

FLOWER AND FLOWER BUD

Blooming habit: Recurrent.

Flower bud:

*Size*.—Upon opening, 40 mm in length from base of receptacle to distal end of bud and 30 mm diameter at its widest point.

*Bud form*.—Long. Pointed ovoid.

*Bud color*.—As sepals first unfold, bud color is Violet Group 85C. When ¼ open, the upper surface of petals is Violet Group 85B, and the lower surface is Violet Group 85C. Marginal zone of guard petals Red-Purple Group 67A to 67B. Middle zone of guard petal is Purple Group 76A and 76B. Basal zone is Yellow-Green Group 154A.

*Sepals*.—Color: Upper surface Green Group 138C. Lower surface Green Group 138B. With intonations of Greyed-Purple Group 184B. Size: Average 12-15 mm (l)×8 mm (w). Shape: There are three lightly appendaged sepals and two unappendaged sepals. Weak foliaceous appendages on three of the five sepals. Apex: Cirrose. Base: Flat at union with receptacle. Quantity: Five. Surface texture: Upper side: Dense pubescence. Lower surface: Very light pubescence. Margins: Pubescent with limited stipitate glands at base and on foliaceous appendages.

Receptacle:

*Surface*.—Shiny, very smooth.

*Color*.—Yellow-Green Group 146C.

*Shape*.—Urn-shaped.

*Size*.—15 mm (h)×15 mm (w).

Peduncle:

*Surface*.—Generally smooth, limited pubescence and occasional stipitate glands.

*Length*.—50 to 60 mm average length.

*Diameter*.—3 to 5 mm average diameter.

*Color*.—Yellow-Green Group 146D.

*Strength*.—Strong.

*Borne*.—Multiple flower buds per stem, generally 1 to 5.

Flower bloom:

*Fragrance*.—Light. Fruity.

*Duration*.—On the plant 3-5 days. As a cut flower, 2 to 3 days. Senesced petals drop away cleanly.

*Size*.—Medium. When open, the average flower diameter is 60 to 80 mm and the average flower height is 35-40 mm.

*Form*.—Shape of flower when viewed from the side: Upon opening, upper part: Flat. Upon opening, lower part: Flattened convex. Open flower, upper part: Flat. Open flower, lower part: Convex.

Color:

*Upon opening, petals*.—Outermost petals: Outer Side: Violet Group 84D. Inner Side: Violet Group 85C. Innermost petals: Outer Side: Violet Group 84C. Inner Side: Purple Group 77B.

*Upon opening, basal petal spots*.—Basal petal spot, outermost petals: Outer Side: Yellow Group 2A. Inner Side: Yellow Group 2A. Basal petal spot, innermost petals: Outer Side: Yellow Group 1A. Inner Side: Yellow Group 2A.

*After opening, petals*.—Outermost petals: Outer Side: Violet Group 85D. Inner Side: Violet Group 85B. Innermost petals: Outer Side: Violet Group 84B. Inner Side: Purple-Violet Group 82D.

*After opening, basal petal spots*.—Basal petal spot, outermost petals: Outer Side: Yellow Group 3B. Inner Side: Yellow Group 3B Basal petal spot, innermost petals: Outer Side: Yellow Group 2B. Inner Side: Yellow Group 2A.

General tonality: On open flower Violet Group 85A to 85B. No change in the general tonality at the end of the 3rd day. Afterwards, general tonality is Violet Group 85D.

Petals:

*Petal count*.—Very Double.

*Average range*.—Approximately 70-75 petals under normal conditions.

*Petal reflex*.—Petals reflex strongly.

*Petal edge*.—Repand to entire.

*Petal shape*.—Entire petal: Ovate to broadly obovate. Apex: Apiculate. Base: Obtuse.

*Petal size*.—50-60 mm (l)×35-40 mm (w).

*Thickness*.—Thin.

*Petal arrangement*.—Not formal.

Petaloids: Usually a few present.

*Petaloid count*.—Average of 3-5 per flower.

*Petaloid size*.—Petaloids are 5-6 mm long and 2-4 mm wide.

*Petaloid color*.—Color of inner side is Purple Group N77B. Color of outer side is Purple Group N77D.

*Petaloid texture*.—Smooth.

*Margins*.—Repand to entire.

*Petaloid shape*.—Overall: Deltoid. Apex: Irregular. Base: Deltoid.

Reproductive organs:

*Pistils*.—Approximately 10-12 present. Stigmas: Location: Slightly inferior in position to anthers. Color: Greyed-Orange Group 164C. Styles: Length: 10 mm long. Color: Yellow-Green Group 145C.

*Stamens*.—Approximately 40 on average and regularly arranged. Anthers: Size: Average 1 mm (l)×0.5 mm (w). Pollen: Generally present. Color: Greyed-Orange Group 164B. Filaments: Color: Yellow Group 5C. Length: 8-10 mm.

THE PLANT

Growth: Moderate Growth.

Plant habit: Upright to bushy habit. When grown as a field grown plant, the average plant height is 80 cm and the average plant width is 40 cm.

Stems:

*Stem color*.—Young wood: Yellow-Green Group 146C. Older wood: Yellow-Green Group 146A to 146B.

*Stem surface*.—Young wood: Smooth. Older wood: Smooth.

Prickles: Present.

*Incidence*.—Average of 5 per each 10 cm of stem.

*Size*.—Average length: 5 mm.

*Color*.—Immature prickles: Yellow-Green Group 152D. Mature prickles: Greyed-Red Group 178A. Senescing to Greyed-Orange Group 176B.

*Shape*.—Deeply concave.

Leaves and leaflets: Normally 5 leaflets on normal leaves in middle of the stem.

*Venation pattern*.—Pyramidal net pattern.

*Leaf size*.—120 mm (l)×120 mm (w).

*Abundance*.—Average.

*Texture*.—Thick. Upper side of leaflet: Semi-glossy, smooth. Under side of leaflet: Matte, smooth.

*Color, mature foliage*.—Upper Leaf Surface: Yellow-Green Group 146B. Lower Leaf Surface: Yellow-Green Group 146B.

*Color, juvenile foliage*.—Upper Leaf Surface: Green Group 137A. Lower Leaf Surface: Yellow-Green Group 146B.

*Anthocyanin intonation*.—Present. Intonations present on immature leaves, stems, stipules, petioles, and prickles. Color is Greyed-Purple Group 183A.

Stipules:

*Size*.—10 mm long. 3 mm between the tips of the stipule.

*Stipule color*.—Yellow-Green Group 146A.

*Anthocyanin*.—Greyed-Red Group 182A.

*Stipitate glands*.—Moderate numbers present on underside.

*Margins*.—Smooth.

*Shape*.—Apex: Apiculate. Base: Flat.

Petiole:

*Length*.—Average 10 mm.

*Diameter*.—Average 2-3 mm.

*Petiole color*.—Yellow-Green Group 146D.

*Underneath*.—Small prickles. Stipitate glands and pubescence present.

*Margins*.—With stipitate glands.

*Anthocyanin*.—Greyed-Red Group 182B.

Petiole rachis:

*Length*.—Average 20 mm.

*Diameter*.—Average 2 mm.

*Color*.—Yellow-Green Group 146C.

*Margins*.—With stipitate glands.

Leaflets:

*Size*.—Average size of the terminal leaflet is 65 mm (l)×45 mm (w).

*Shape*.—Entire leaflet: Obtuse to ovate. Base: Ovate. Apex: Obtuse.

*Margins*.—Finely serrated.

*Surface*.—Upper: Semi-glossy and smooth. Lower: Matte and smooth.

*Texture*.—Leathery.

Hips/seed formation: None observed.

Winter hardiness: To date, the variety has been grown successfully in Zone 5.

Disease resistance: Excellent resistance to Powdery mildew (*Sphaerotheca pannosa*), rust (*Phragmidium disciflorum*), blackspot (*Diplocarpon rosae*), and *Botrytis* (*Botrytis cinerea*) diseases under normal growing conditions.

I claim:

1. A new and distinct variety of rose plant, as described and illustrated herein.

* * * * *

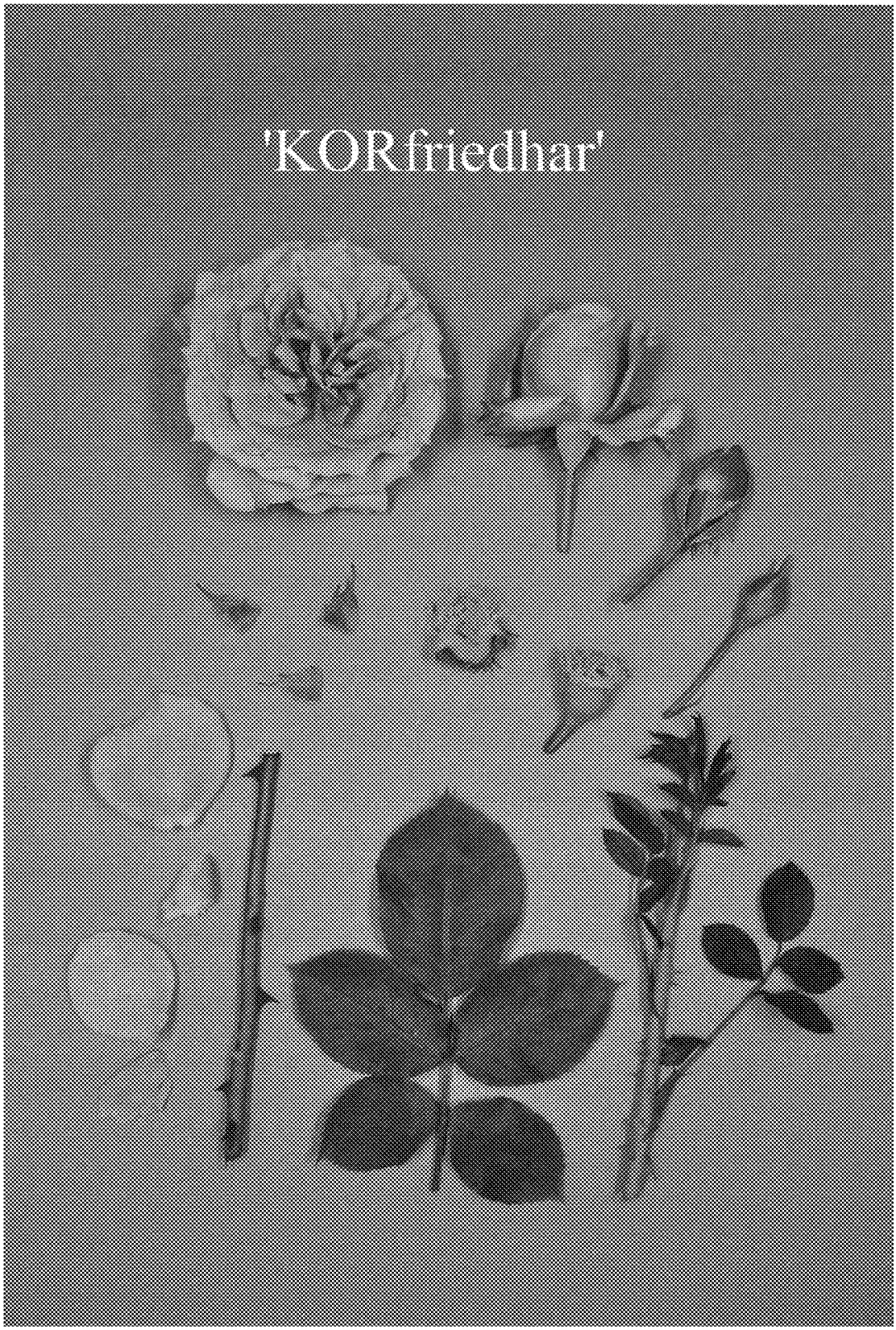
'KORfriedhar'